United States Patent
Schmitz

(10) Patent No.: US 10,239,284 B2
(45) Date of Patent: Mar. 26, 2019

(54) MELTFUSION BONDED ABSORBANT STRUCTURE COMPRISING FIBRES AND SUPERABSORBANT PARTICLES METHOD FOR MANUFACTURING SUCH STRUCTURE

(71) Applicants: CONCEPTS FOR SUCCESS (C4S) E.K., Euskirchen (DE); Christoph Schmitz, Euskirchen (DE)

(72) Inventor: Christoph Schmitz, Euskirchen (DE)

( * ) Notice: Subject to any disclaimer, the term of this patent is extended or adjusted under 35 U.S.C. 154(b) by 359 days.

(21) Appl. No.: 14/411,889

(22) PCT Filed: Jun. 28, 2013

(86) PCT No.: PCT/EP2013/063595
§ 371 (c)(1),
(2) Date: Dec. 29, 2014

(87) PCT Pub. No.: WO2014/001487
PCT Pub. Date: Jan. 3, 2014

(65) Prior Publication Data
US 2015/0164699 A1    Jun. 18, 2015

(30) Foreign Application Priority Data

Jun. 29, 2012 (GB) .................................. 1211577.0
Aug. 19, 2012 (GB) .................................. 1216670.8
Nov. 16, 2012 (GB) .................................. 1220625.6

(51) Int. Cl.
*B32B 3/10*    (2006.01)
*B32B 7/04*    (2019.01)
(Continued)

(52) U.S. Cl.
CPC ........ *B32B 7/045* (2013.01); *A61F 13/15634* (2013.01); *A61F 13/15658* (2013.01); *A61F 13/15699* (2013.01); *A61F 13/15731* (2013.01); *A61F 13/533* (2013.01); *A61F 13/5323* (2013.01); *B29C 65/087* (2013.01); *B29C 66/1122* (2013.01); *B29C 66/21* (2013.01); *B29C 66/45* (2013.01); *B29C 66/7373* (2013.01); *B29C 66/81453* (2013.01); *B29C 66/83411* (2013.01); *B29C 66/83511* (2013.01); *B32B 5/00* (2013.01); *B32B 37/0076* (2013.01); *B32B 37/0084* (2013.01); *B32B 37/06* (2013.01); *B32B 37/10* (2013.01); *B32B 37/18* (2013.01); *D04H 1/555* (2013.01);
(Continued)

(58) Field of Classification Search
None
See application file for complete search history.

(56) References Cited

U.S. PATENT DOCUMENTS

| 5,411,497 A | 5/1995 | Tanzer et al. |
| 2002/0016122 A1* | 2/2002 | Curro .................. A47L 1/15 442/381 |
| 2008/0038504 A1* | 2/2008 | Manabe ............. A61F 13/537 428/71 |

FOREIGN PATENT DOCUMENTS

| EP | 0297411 A1 | 1/1989 |
| EP | 0339461 A1 | 11/1989 |

(Continued)

*Primary Examiner* — Christopher Polley

(57) ABSTRACT

The present invention is an absorbent structure comprising a fibrous matrix (110), meltfusionable material and superabsorbent polymer particles (140). The absorbent structure is bonded by a meltfusion bond point (200) pattern, which is preferably created by ultrasonic welding.

12 Claims, 4 Drawing Sheets

(51) Int. Cl.

| | | |
|---|---|---|
| *A61F 13/533* | (2006.01) | |
| *B29C 65/08* | (2006.01) | |
| *B29C 65/00* | (2006.01) | |
| *B32B 37/10* | (2006.01) | |
| *D04H 1/555* | (2012.01) | |
| *D04H 1/559* | (2012.01) | |
| *A61F 13/532* | (2006.01) | |
| *B32B 5/00* | (2006.01) | |
| *B32B 37/06* | (2006.01) | |
| *B32B 37/18* | (2006.01) | |
| *B29L 31/48* | (2006.01) | |
| *B32B 37/00* | (2006.01) | |
| *A61F 13/15* | (2006.01) | |
| *A61F 13/53* | (2006.01) | |
| *B32B 37/24* | (2006.01) | |

(52) U.S. Cl.
CPC .... *D04H 1/559* (2013.01); *A61F 2013/15861* (2013.01); *A61F 2013/15869* (2013.01); *A61F 2013/530532* (2013.01); *A61F 2013/530554* (2013.01); *A61F 2013/530562* (2013.01); *A61F 2013/530576* (2013.01); *B29C 66/71* (2013.01); *B29C 66/729* (2013.01); *B29C 66/7294* (2013.01); *B29C 66/73921* (2013.01); *B29L 2031/4878* (2013.01); *B32B 37/0053* (2013.01); *B32B 37/24* (2013.01); *B32B 2250/02* (2013.01); *B32B 2305/026* (2013.01); *B32B 2305/20* (2013.01); *B32B 2307/726* (2013.01); *B32B 2555/02* (2013.01); *Y10T 156/17* (2015.01); *Y10T 428/24826* (2015.01); *Y10T 428/24851* (2015.01)

(56) References Cited

FOREIGN PATENT DOCUMENTS

| | | |
|---|---|---|
| EP | 0752892 A1 | 1/1997 |
| EP | 1199059 A1 | 4/2002 |
| EP | 1621165 A1 | 2/2006 |
| EP | 1982678 A1 | 10/2008 |
| JP | 2008/125602 A | 6/2008 |
| WO | 2007/107846 A1 | 9/2007 |
| WO | 2012/048878 A1 | 4/2012 |
| WO | WO 2012042055 A1 * 4/2012 ............. B29C 65/08 |

* cited by examiner

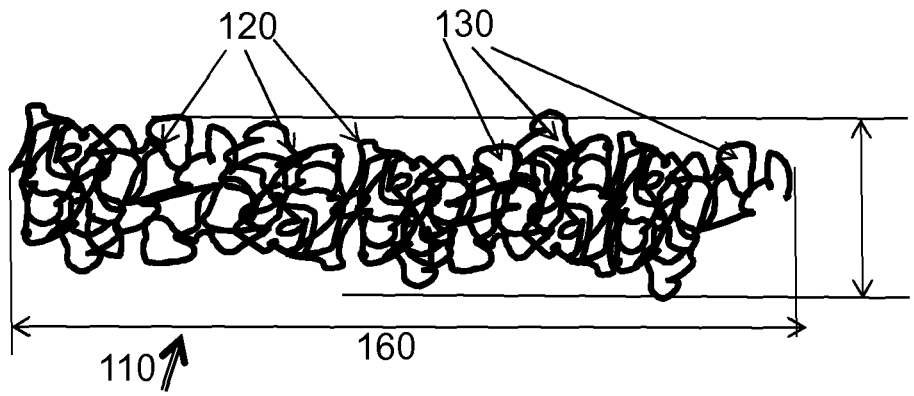
Fig. 1A
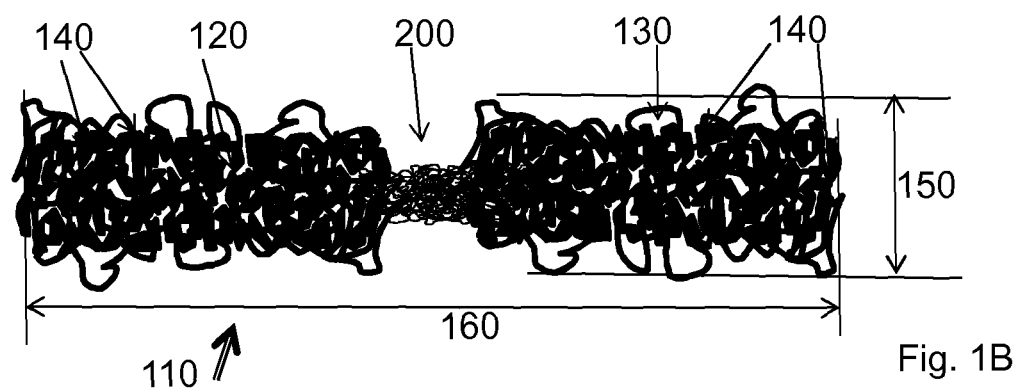
Fig. 1B
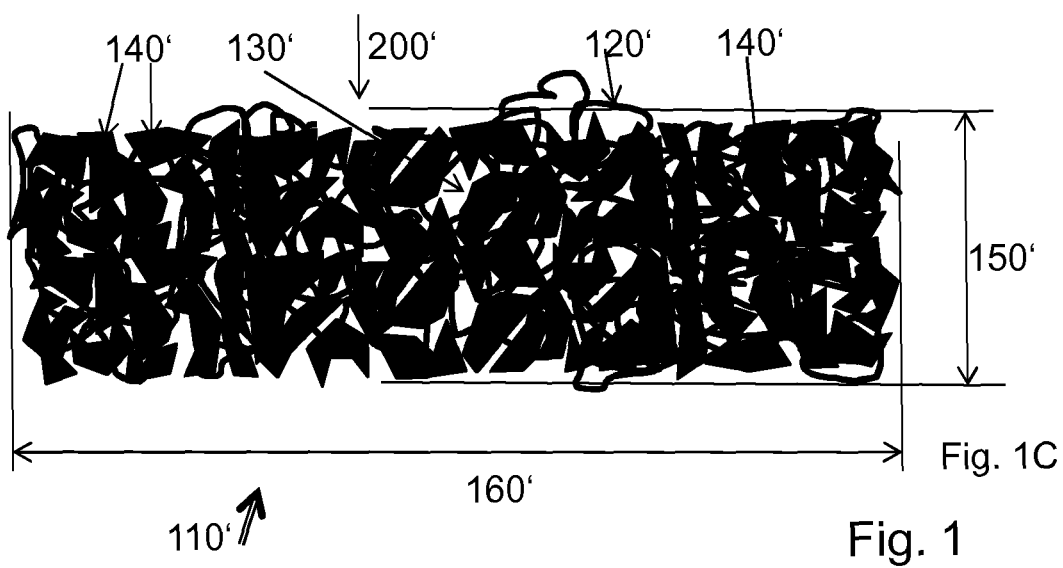
Fig. 1C
Fig. 1

MELTFUSION BONDED ABSORBANT STRUCTURE COMPRISING FIBRES AND SUPERABSORBANT PARTICLES METHOD FOR MANUFACTURING SUCH STRUCTURE

CROSS-REFERENCE TO RELATED APPLICATIONS

This application is a U.S. national phase application under 35 U.S.C. § 37 based upon co-pending International Application No. PCT/EP2013/063595. Additionally, this U.S. national phase application claims the benefit of priority of co-pending International Application No. PCT/EP2013/063595 filed on Jun. 28, 2013. The entire disclosure of the prior application is incorporated herein by reference. The international application was published on Jan. 3, 2014 under Publication Number WO 2014/001487 A1.

FIELD OF THE INVENTION

The present invention is a liquid absorbent structure comprising superabsorbent polymer, such as superabsorbent particles, which are well immobilized at least in a dry state without being restricted upon swelling. Such structures can be used to absorb bodily exudates such as in absorbent articles such as baby diapers, adult incontinence articles, and the like. In a different aspect, the present invention is a manufacturing method for providing such structures.

BACKGROUND

Liquid absorbent structures are well known in the art such as for the application in absorbent articles such as baby or adult incontinence diapers, feminine hygiene articles, but also for absorbing liquids in food packages or for other liquid spills.

It is also well known to use superabsorbent polymers (SAP). Whilst such materials provide improved liquid storage capacity as compared to the fibrous materials typically used before, they provided challenges to the designer of absorbent structures.

For example, such SAP are typically provided as particles. Thus, unless certain measures are taken, there is a risk of such particles dislocating, either during manufacturing, storage, or use, thereby at least altering the performance characteristics of the structure if not spilling out of the structures undesirably.

Further, even the most advanced versions of SAP are still prone to the "gel blocking" phenomenon, i.e. when used at high concentrations or as pure particle accumulation, some of the SAP can swell up whilst hindering liquid to reach other SAP particles.

There has been a plethora of approaches to overcome these and other challenges.

Starting from fibrous, mostly cellulosic, structures with relatively small amounts of SAP distributed therein, the properties of the SAP have ongoingly been improved so as to allow concentrations of about 60% by weight without substantial gel blocking occurring. Also, at such concentrations the fibrous matrix dominates the structures and holds the particles sufficiently in place, see e.g., EP0339461 (K-C; Kellenberger) or EP0752892A1 (P&G; Goldman).

Further it has been recognized and described in EP1982678 (P&G) that absorbent structures should not only immobilize the particles in the dry state, but that also the liquid loaded structure should immobilize the swollen gel.

In order to increase the relative amount of SAP in an absorbent structure, the cellulosic fibres were at least partly removed and replaced by synthetic binder.

An early approach is described in EP0297411A1 (Peaudouce, Koczab) by placing SAP particles in a matrix of synthetic fibres and thermobonding the structure along a bonding pattern with continuous bond lines forming a hexagonal pattern. The thermobonding has been described to negatively impact the absorbency properties of the structure.

EP1199059B1 (U-C; Onishi) describes the mixing of fibres exhibiting a lower and a higher melting point such that upon application of energy a three-dimensional fibre matrix is created.

In JP2008/125602 a structure is described wherein two types of fibres with particles intermixed are permanently bonded.

Further approaches position SAP particle accumulations in "pockets" sandwiched between webs. The particles can be immobilized such as by circumscribing the pockets with bonded regions, either by adhesive means or by thermobonding, see e.g., In EP1621165A1 (P&G; Blessing) structures are described that rely on adhesive bonds and aim by a rather complex process to keep the bonding regions between premetered SAP particle accumulations free of SAP particles.

WO2012/048878 (Romanova; van der Maele) shows premetering of SAP particle accumulations and thermobonding of the webs. Even though particular and complex measures, such as specific air blower arrangement, are taken to keep the boding regions free from particles, the bonding is sensitive to such contamination.

The description of the copending application GB12166708 (filed on Sep. 19, 2012; unpublished; C4S; Schmitz), provides an improved sandwich structure with particulate SAP pockets positioned between two ultrasonically bonded webs. The particular method ensures that the bond points are free of particles and thus the bond points provide strong bonds between the sandwich webs.

As SAP material swells upon imbibing liquids, it expands in volume, which has to be reflected in the structure.

Thus in U.S. Pat. No. 5,411,497 (K-C; Tanzer) structures are described with water-sensitive attachment, such that upon the first wetting of the structure such attachments de-bond and the SAP can swell more freely.

Notwithstanding the above approaches, there is still a need for providing absorbent structures which provide good dry and wet immobilization whilst not unduly deteriorating the absorbency properties of the structure compared to the ingoing materials.

Even further there is a need for providing a simple method for manufacturing such structures, without a need for dosed deposition of material pockets as described in the above mentioned publications.

SUMMARY

The present invention is an absorbent structure exhibiting an x-, y-, and z-direction and comprising
 fibres forming a fibrous matrix having an x-, y-, and thickness or z-extension;
 superabsorbent polymer (SAP) particles which are capable of exerting an expansion force upon swelling upon absorption of a liquid and which are positioned within the pores of the fibrous matrix;

and meltfusion bond points arranged in an x-y-directionally extending bonding pattern, penetrating at least partially z-directionally through the fibrous matrix, whereby the bond points exhibit a de-bonding strength up to which the bond point holds and above which the bond point de-bonds, and whereby the matrix with the particles exhibits an overall thickness when dry. The fibrous matrix comprising the particles is capable of increasing its overall thickness upon swelling of the SAP particles whereby the expansion force exerted by the SAP particles to the bond points is higher than the de-bonding strength of the bond points such that the bond points de-bond upon swelling of the SAP particles. Preferably, the bond points are essentially water-insensitive.

The bonding pattern of the absorbent may satisfy one or more of the following conditions:
the bond points have a bond point size of from about 0.1 mm$^2$ to about 20 mm$^2$;
the bond points exhibit an aspect ratio of their long axis to their short axis of at least 1.05 to 1, preferably of at least 1.1 to 1;
the bond points exhibit an ellipsoidal shape;
the number of bond points in the pattern is from one bond point per 9 cm$^2$ to 1 bond point per 9 mm$^2$;
the bonding pattern comprises one or more sub-pattern;
at least two bonding patterns form a macro pattern.

The median pore size of the fibrous matrix is preferably such that is larger than the median particle size of SAP particles. The median the pore size of the fibrous matrix may be less than 3.5 times, less than 3.3 times smaller than the median particle size of the SAP particles.

The fibres of the fibrous matrix may reposition upon swelling of the SAP and SAP particles may re-arrange upon swelling so as to allow non-isotropic expansion of the structure preferentially in z-direction.

An absorbent structure according may comprise on the basis of the weight the absorbent structure
SAP at at least 60%, preferably more than 70%, more preferably more than 80%;
meltfusionable material at at least 5%;
fibres at at least 5%, preferably more than 10%;
wherein the meltfusionable material may be unitary with the fibres.

The SAP particles may be present in the absorbent structure at a local basis weight of at least 50 g/m$^2$, preferably more than 70 g/m$^2$, more preferably more than 100 g/m$^2$, even more preferably more than 200 g/m$^2$. The SAP particles are preferably essentially unbonded to the fibres.

The fibrous matrix of the absorbent structure may exhibit a pore size gradient or the structure may comprise a cover or carrier web. The meltfusionable material or the fibres of the absorbent structure may comprise material, which is thermoplastic, preferably a polyolefin, more preferably polyethylene or polypropylene. The fibres of the fibrous matrix of the absorbent structure may comprise a thermoplastic material exhibiting a softening temperature higher than the one of the meltfusionable material. The meltfusionable material and the fibres of the absorbent structure may be essentially unitary.

The absorbent structure may further comprise one or more of the following:
one or more cover web(s) positioned parallel to the x-y-directionally extending surface of the structure, optionally being connected thereto, optionally by the meltfusionable bond points;
one or more secondary containment means, circumscribing the absorbent structure x-y-directionally, preferably a circumferential bonding exhibiting a bond strength higher than the bond strength of the meltfusionable bonding points; expansion aiding means, preferably circumferential fold lines or pop-open—lines
liquid handling elements.

The absorbent structure may be comprised in an absorbent article, which may further comprising one or more of the following elements:
further liquid handling elements;
liquid retention means such as liquid impermeable layers;
chassis elements for allowing fixation of the article on a wearer.

The present invention also relates to a method for the manufacture of an absorbent structure, comprising
fibres forming a fibrous matrix having an x-, y-, and thickness or z-directional extension;
superabsorbent polymer (SAP) particles which are capable of exerting an expansion force upon swelling upon absorption of a liquid and which are positioned within the pores of the fibrous matrix;
and meltfusion bond points arranged in an x-y-directionally extending bonding pattern, penetrating at least partially z-directionally through the fibrous matrix.

The method comprising the steps of
providing a fibrous matrix;
providing SAP particles;
positioning the SAP particles in interfibre pores of the matrix;
providing a support structure, preferably in the form of a flexible helical anvil;
positioning the fibrous matrix with the SAP particles on the support structure;
applying energy to the absorbent structure to form meltfusion points in a predetermined pattern determined by the support structure.

Preferably, the energy is ultrasonic energy.

The meltfusion bond points form a distinct x-y-directional bond point pattern, preferably satisfying at least one of the following conditions:
the bond points have a bond point size of from about 0.1 mm$^2$ to about 20 mm$^2$;
the bond points exhibit an aspect ratio of their long axis to their short axis of at least 1.05 to 1, preferably of at least 1.1 to 1;
the bond points exhibit an ellipsoidal shape;
the number of bond points in the pattern is from one bond point per 9 cm$^2$ to 1 bond point per 9 mm$^2$;
the bonding pattern comprises one or more sub-pattern.

Optionally, the fibrous matrix is provided as one or more prebonded web(s).

The positioning of the particles in the fibrous matrix may be aided by an embedding aiding means preferably comprising one or more of the following elements
vacuum;
tentering x- or y-directionally;
mechanically activating between two smooth, profiled or interdigitizing rolls;
shaking or vibrating.

The method may further comprise one or more of the following steps of
applying one or more cover web(s) positioned parallel to the x-y-directionally extending surface of the structure, optionally being connected thereto, optionally by the meltfusionable bond points;
applying one or more secondary containment means, circumscribing the absorbent structure x-y-directionally, preferably a circumferential bonding exhibiting a bond strength higher than the bond strength of the meltfusionable bonding points; or applying an expansion aiding means, preferably circumferential fold lines or pop-open—lines;

providing the SAP particles in an essentially continuous stream, which is modulated, preferably interrupted, before said particles are positioned in the interfibre pores.

BRIEF DESCRIPTION OF THE FIGURES

FIG. 1 A to C describe schematically the arrangement of fibres, pores and SAP particles in a structure according to the present invention.

Figure 2:
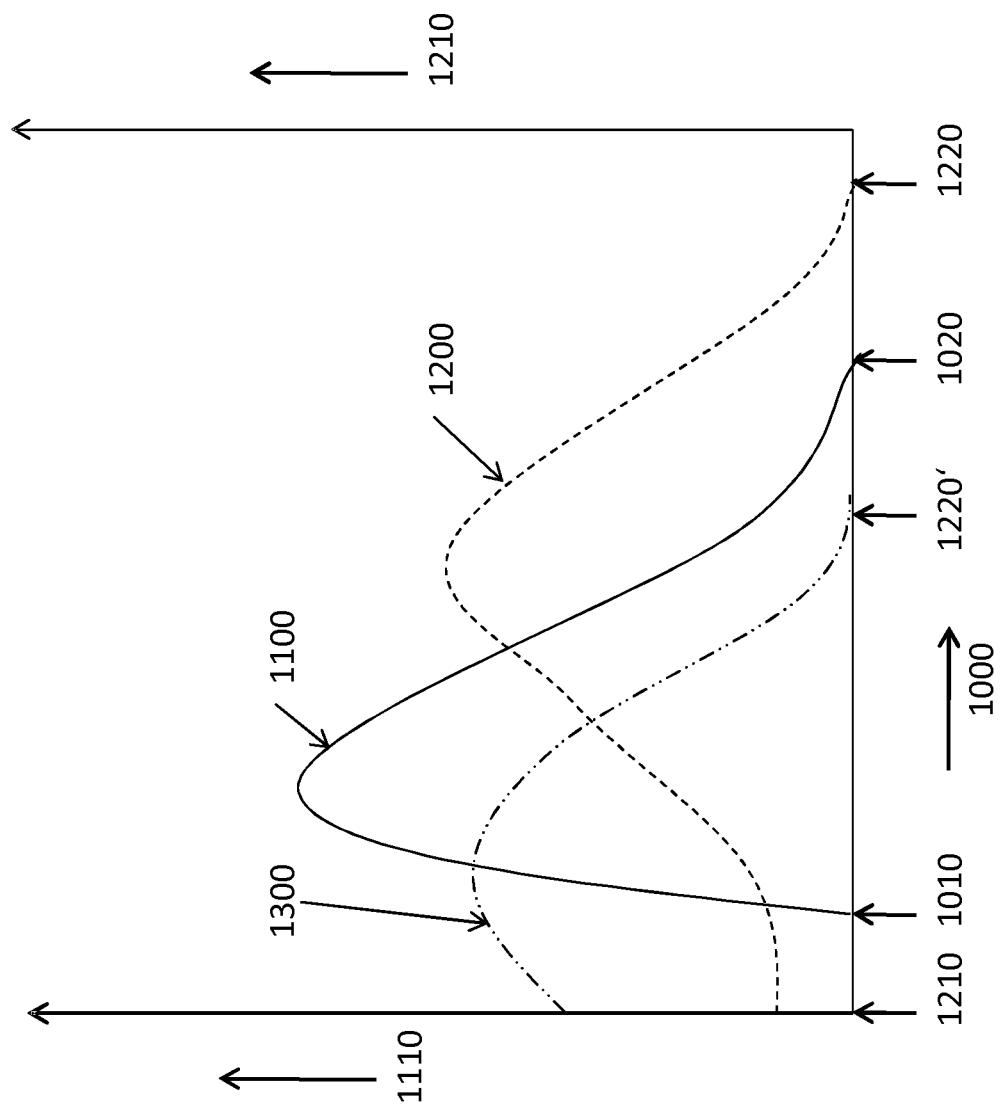
FIG. 2 depicts schematically particle and pore size distribution for explaining their relative size.

Equal numerals refer to same or equivalent elements.

DETAILED DESCRIPTION

Within the present context, structures, fibrous matrices or webs as well as process aspects are described by using Cartesian coordinates, such that the x-direction or machine direction corresponds to the length, the y- or cross-machine direction corresponds to the width, and the z-direction to the thickness.

Unless expressly stated, the term pore size refers to interfibre pores, i.e. the space between fibres, regardless if the space is void or completely or partly taken by SAP particles.

Unless otherwise expressly stated, all percentages refer to weight percentages.

In a first aspect the present invention is a liquid absorbent structure for receiving and retaining aqueous fluids.

Thus, an important application of the present invention relates to structures that are useful in absorbent articles such as baby diaper, adult incontinence, feminine hygiene, but also for food pads, bibs, swabs, and the like.

The absorbent structures according to the present invention comprise a fibrous matrix with superabsorbent polymer (SAP) particles positioned in interfibre voids or pores of the structure. The absorbent structure is bonded by thermofusion or meltfusion bonds, which exhibit a predetermined bond strength. Once the structure is loaded with liquids and the SAP particles begin to swell, this swelling of particles will de-bond the bonding and thusly allow the particles to further swell without being restricted by the bonding of the structure. Such a structure immobilizes the SAP particles in a dry state but due to the fibres between the swollen particles also in a wet state.

Thus SAP particles are held in the structure in the dry state by the meltfusion bond points as primary dry containment means and the fibres of the fibrous matrix as secondary containment means. Upon wetting, the fibres function as primary containment means, preferably supported by a circumferential fixation as secondary containment means.

The absorbent structures according to the present invention comprise superabsorbent polymers. Superabsorbent polymers (SAP) are often also referred to as "super absorbent", "super absorbent material", "absorbent gelling material", hydro gel, or "absorbent polymer material", or "AGM", all referring to partially cross-linked polymeric materials, which can absorb water whilst they are swelling to form a gel.

Suitable superabsorbent materials useful in the present invention include superabsorbent particles as are known in the art. Generally, superabsorbent materials include water-swellable, generally water insoluble materials capable of absorbing at least about 10 times their weight in water. More specifically, superabsorbent materials are capable of absorbing as much as 20 times their weight in water, and more specifically 50 times, 100 times, or even up to 300 times or more their weight in water (or other aqueous medium). Superabsorbent materials may be formed from organic material which may include natural materials such as agar, pectin, and guar gum, as well as synthetic materials such as synthetic hydrogel polymers. Synthetic hydrogel polymers include, for example, carboxymethylcellulose, alkali metal salts of polyacrylic acid and its copolymers, polyacrylamides, polyvinyl alcohol, ethylene maleic anhydride copolymers, polyvinyl ethers, hydroxypropylcellulose, hydroxypropyl acrylate, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are suitably lightly crosslinked to render the material substantially water insoluble. Crosslinking may, for example, be by irradiation or by covalent, ionic, Van der Waals, or hydrogen bonding. Suitable materials are available from various commercial producer or vendors, such as the Nippon Shokubai KK (Himeji, Japan), Evonik-Stockhausen GmbH (Marl, Germany), and BASF SE (Ludwigshafen, Germany), Danson (Yixing, China), EKOTEC GmbH (Haan, Germany) and many more. It is important that the SAP particles exert forces upon swelling. Such swelling forces correlate with SAP particles ability of swelling against an applied pressure. A particularly preferred superabsorbent material has an Absorption Against Pressure (AAP) of at least about 20 g/g and a Saline Flow Conductivity (SFC) that is greater than about $30 \times 10^{-7}$ ($cm^3$ seconds)/g. Preferably, AAP is greater than about 23 g/g, more preferably greater than about 25 g/g, as measured according to the methods described in the TEST METHODS section below These superabsorbent materials are preferably used at an average basis weight of the absorbent structure of at least about 200 $g/m^2$, preferably at least about 400 $g/m^2$, more preferably at least about 600 $g/m^2$, averaged over a representative area of the absorbent structure. In order to maintain satisfactory flexibility, the basis weight is also less than about 2000 $g/m^2$.

The particles preferably exhibit a particle size of between 50 and 1500 μm, Often, the median particle diameter ranges between about 200 μm and about 800 μm.

Typical materials are commercially available under the trade designation SXM 9170 (EVONIK-Stockhausen, Germany) or EK-X EN 67 (EKOTEC GmbH, Germany).

The absorbent structure comprises meltfusionable material. Within the present context, the term "meltfusionable" refers to materials, which at increasing temperatures become soft and plastically deformable and eventually molten, thusly being able to be deformed to bond to themselves or to other material, which may remain essentially non-molten or not plastically deformed. Upon cooling, the meltfusionable material returns to an essentially solid state. Preferably, the solidified meltfusionable material is not tacky and exhibits no significant adhesive properties. Note that although the term "melting" as commonly used in the art includes "softening" of the thermoplastic material such that it is not truly melted to the point of liquefaction but merely to the point where the outermost surface of the thermoplastic material begins to soften and become tacky.

Preferably, the melting point of the meltfusionable material will be less than about 190° C., and preferably between about 75° C. and about 175° C. In any event, the melting point of the meltfusionable material should be no lower than the temperature at which the thermally bonded absorbent structures, when used in absorbent articles, are likely to be stored. The melting point of the meltfusionable material is typically no lower than about 50° C.

The meltfusionable materials can be made from a variety of thermoplastic polymers, including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloridevinyl acetate, and the like. Thermoplastic elastomers such as styrenic block copolymers; elastomeric polyolefins or blends thereof, elastomeric alloys, or other thermoplastic polyurethanes, copolyester, or polyamides can be employed, but are less preferred than materials which comprising non-elastic polyolefins, in particular polypropylene.

The meltfusionable material may be introduced into the absorbent structure by various ways, as long as it ensured that the materials are made available at the bond sites upon bonding.

Thus they may be mixed with other material forming the absorbent structure prior to executing the meltfusion bonding step. To this end, the meltfusionable material may be in a particulate, or fibrous, or other form like films, optionally apertured films. The above mentioned bicomponent fibres may be a particular execution of such combination, wherein the fibrous matrix and the meltfusionable material are identical.

The meltfusionable material may be distributed homogeneously. It may be applied in a concentration gradient throughout the z-direction of the structure. The meltfusionable material may also be employed in an x-y-directionally extending pattern, optionally including sub- and/or macro-patterns.

Additionally or alternatively the meltfusionable material may be added via an additional layer, such as a web, such as a non-woven or a film, on one or both x-y-directionally extending surfaces of the absorbent structure.

The absorbent structure according to the present invention comprises fibres for forming a fibrous matrix. "Fibre" refers to a continuous or discontinuous member having a high ratio of length to diameter or width. Thus, a fibre may be a filament, a thread, a strand, a yarn, or any other member or combination of these members.

The term "fibres" also includes fibres, which over their length appear partly molten (such as when a fibre extends through a bonding region) or which are partly molten across the cross-section of the fibres, such as when a fibre is attached only superficially whilst maintaining its fibrous shape, such as when the sheath material of a bicomponent fibre is molten, but the fibre core material not.

Fibres useful for the present invention may be natural ones, such as modified or unmodified cellulose fibres, or synthetic ("man made") fibres including fibres as made from natural ingredients such as without limitation viscose/rayon.

Preferred materials for synthetic fibres are thermoplastic materials, such as described hereinbefore for meltfusionable materials.

Thus, suitable thermoplastic fibres can be made from a single polymer (monocomponent fibres), or can be made from more than one polymer (e.g., bicomponent fibres). As used herein, the term "bicomponent fibres" refers to thermoplastic fibres that comprise a core fibre made from one polymer that is encased within a thermoplastic sheath made from a different polymer. The polymer comprising the sheath often melts at a different, typically lower, temperature than the polymer comprising the core. As a result, these bicomponent fibres provide thermal bonding due to melting of the sheath polymer, while retaining the desirable strength characteristics of the core polymer.

Suitable bicomponent fibres for use in the present invention can include sheath/core fibres having the following polymer combinations: polyethylene/polypropylene, polyethylvinylacetate/polypropylene, polyethylene/polyester, polypropylene/polyester, copolyester/polyester, and the like.

Suitable fibres may be limited length fibres, such as knows as staple fibres, but also natural fibres like cellulose fibres. Typically such natural or staple fibres exhibit a fibre length from about 0.1 to 15 cm. often from about 2 to 7 cm.

Suitable fibres may be substantially continuous fibres, which are not cut from their original length prior to being formed into a nonwoven web or fabric or are otherwise integrated into the absorbent structure. Substantially continuous fibres may have average lengths ranging from greater than about 15 centimeters to more than one meter, and up to the length of the web or absorbent matrix being formed.

Spunmelt fibres are made into a fibrous matrix in one continuous process. Fibres are spun and then directly dispersed into a fibrous matrix or web by deflectors or can be directed with air streams thereto. It should be noted that the term "spunmelting" includes different methods such as spunbonding, meltblowing, or advanced meltblowing, referring to techniques combining elements of spunbonding and meltblowing (see e.g. BIAX® fibres). Spunmelting may provide essentially endless fibres, such as resulting from the spunbonding process, or fibres exhibiting a limited length, such as resulting from the meltblowing process with a fibre length of typically 30 mm to about 100 mm or more.

The fibres useful in the present invention may generally have a thickness ranging from about less than about 1 to over 15 dTex. Mostly the dTex of the fibres will range between about 1.5 and 7, though finer or even nano-fibres may be included.

Suitable fibres may be crimped and have a crimp count of at least two crimps per centimeter and a percent crimp of at least about 15%, preferably at least about 25%. Percent crimp is defined as the difference between the uncrimped length of the fibre (measured after fully straightening a sample fibre without stretching it elastically or plastically) and the crimped length (measured by suspending the sample fibre with a weight attached to one end equal to 2 mg per decitex of the fibre, which straightens the large-radius bends of the fibre) divided by the crimped length and multiplied by 100. Crimped fibres may be staple fibres or result from a process such as spunmelting.

For executing the present invention it is not particularly relevant how the fibrous matrix is formed, as long as the criteria as defined herein are met. Thus the fibres may be laid down to form a fibrous matrix in-line, i.e. during a continuous process during which the absorbent matrix is formed.

Additionally or alternatively, the fibrous matrix may be provided as a preformed and/or prebonded web. The term "web material" refers to a material, which is essentially endless in one direction, i.e. the longitudinal extension, or the length, or the x-direction in Cartesian coordinates relative to the web material. Included in this term is an essentially unlimited sequence of pieces cut or otherwise separated from an essentially endless material. Typically, the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web.

The web may be a "nonwoven" material that is a manufactured sheet or web of directionally or randomly oriented fibres which are first formed into a batt such as by melt-blowing, spunbonding, spunmelting, solvent spinning, electrospinning, carding, film fibrillation, melt-film fibrillation, airlaying, dry-laying, wet laying with staple fibres, and combinations of these processes as known in the art. The nonwoven may be consolidated and pre-bonded together by friction, such as resulting from hydroentangling or needlepunching, cohesion, adhesion or meltfusion bonding, such as between connecting points of neighbouring fibres molten by air-trough bonding, or one or more patterns of bonds and bond impressions created through localized compression and/or application of pressure, heat, ultrasonic or heating energy, or a combination thereof. The basis weight of nonwoven fabrics is usually expressed in grams per square meter (gsm).

The use of hot-melt adhesives for pre-bonding is less preferred, if their melt behaviour interferes with the meltfusion bonding as described herein below.

The fibrous matrix may also be provided by fabrics which are woven, knitted, or stitch-bonded with yarns or filaments, although this may be less preferred if such structures exhibit their typical x-y-directional inhomogeneity.

Such in-line or pre-formed webs should satisfy the general requirements of materials being useful in absorbent structure and—where required—in disposable absorbent articles.

In particular when the absorbent structure is incorporated in articles which undergo significant compression, such as during transportation and storage, it is preferred that the fibrous matrix comprises resilient materials, which also exhibit low tendency of "cold flow". Preferred materials comprise polyester and/or co-polyester. Optionally the structure may comprise different types of fibres in mixed or in a layered arrangement.

It is important that the fibrous matrix exhibits a pore size sufficiently large to accommodate SAP particles. The pore size requirement is dependent on the particle size of the corresponding SAP particles. Considering that the SAP particle size should range between 50 and 1500 μm the pores of the web preferably are adapted thereto and cover a range of up to 1500 μm, but the skilled person will readily realize that not all of the pores need to be that large. A simple criterion for assessing if the pores size and particle size requirements are met is to visually inspect the structures by the naked eye, magnifying glasses or a microscope. If an unloaded web and pure SAP particles are available, a representative sample of the SAP material may be sprinkled over the web at a basis weight ratio of about 70% SAP to 30% web material.

It is important that at least a portion of the SAP particles are positioned within the pores of the matrix. If appropriate measures are taken, such as recycling of material or use of cover and/or carrier materials, some of the SAP particles, in particular larger sized particles, may rest on top of the matrix, i.e. do not penetrate into the matrix, or other SAP particles may penetrate through the matrix.

The skilled reader will readily realize that the pore size of the web has to be considered as the pores between the fibres, i.e. neglecting the particles therein. This can be assessed by optically analysing the composite of fibres and SAP particles in the dry state, such as described in: Digital Image Analysis to Determine Pore Opening Size Distribution of Nonwoven Geotextiles; Aydilek et al.; DOI: 10.1061/(ASCE) 0887-3801 (2002) 16:4 (280). Alternatively, though often more unreliable, the dry particles can be gently removed from the fibrous matrix, and the matrix may be analyzed optically or by other well known pore size determination methods for non-woven materials, such as wetting methods. If available, the pore size can be determined by assessing the web prior to the adding SAP particles by conventional tools, such as the digital method or fluid wetting methods.

A further method can then be applied by selecting several cuts of particles exhibiting a narrow particle size, such as by selecting sieve fractions from a conventional sieve test and observing certain fraction to be retained on the surface of or penetrating through the fibrous matrix.

As will be described in more detail herein below, it should be noted that the pore size requirement should be met at the point in time of adding the SAP. Thus, it is also contemplated that a pre-formed web may be provided with a first pore size that is modified just prior to or after the application of the SAP, such as by tentering or incremental stretching.

The fibrous matrix may comprise regions exhibiting varying pore size distributions. In a first execution, there is a z-directional pore size gradient, such as by gradually layering different fibre types, such as exhibiting different fibre thickness (or decitex). Varying ore size distributions may also be achieved by layering of two or more fibrous matrices.

It is preferred that the pre-formed web is not overly strong pre-bonded. Without wishing to be bound by a theory it is further believed that the fibres in the web should preferably be repositionable relative to each other and to the SAP particles.

Such a repositioning may take place upon the swelling of the SAP such that the particles rearrange themselves in a non-isotropic manner, which requires that the fibrous matrix respectively the fibres therein provide sufficient flexibility.

Such an effect can be achieved by various approaches, which may be applied alone or in combination, such as by using crimped fibres, exhibiting preferably more than about 2 crimps/cm and/or by employing long fibres of at least 5, preferably more than 10 mm length.

A preferred thermoplastic nonwoven can be made of staple fibres, most preferably of staple fibres with a staple length in a range from 5 to 150 mm, most preferably 30 to 100 mm, such as crimped polyester/bicomponent polyester at a basis weight of from about 20 gsm to about 200 gsm at a density of from about 20 to about 100 kg/m$^3$. Suitable materials are commercially available air-through bonded polyester materials, such as Paratherm Loft VTF 273 at 90 gms basis weight from Libeltex, Belgium, or from TEXSUS SPA, Italy.

The absorbent structure according to the present invention comprises SAP particles positioned in a matrix of fibres and bonded by meltfusion bonds.

The fibrous structure may only be bonded by the meltfusion bonds holding the particle loaded structure together. The fibrous structure may be formed in-line and may be a pre-bonded web, such as by a further meltfusion bonding, such as compression or calender bonding, or by other means such as air-through bonding, resin bonding and the like.

The absorbent structure may have an essentially homogenous composition, i.e., the SAP in the meltfusionable material may be evenly distributed among the fibrous matrix.

In a particular execution, the meltfusionable material may be incorporated in the fibres of the fibrous matrix, such as when the fibrous matrix is made of meltfusionable material, or it comprises bicomponent fibres comprising meltfusionable material.

The absorbent structure may have a layered structure. For example, the meltfusionable material may be provided as a separate web, such as a carrier or cover web, often as a nonwoven or in a film form. In this execution, the cover and/or carrier web may provide meltfusionable material, but it may also function for retaining the SAP particles in the absorbent structure.

In a preferred execution, the cover or carrier web is a nonwoven material, such as a carded, wet- or airlaid web, or a melts-spun web, which may be a single layer or which may comprise several layers of melt-spun, spunbonded, and/or melt-blown webs, and may be denoted as "SMS", "SMMS", SSMMS, . . . webs, wherein "S" stands for spunbonding and "M" for melt-blowing. Preferably, such cover or carrier webs exhibit a pore size so as to prevent SAP particles to penetrate through.

In another execution of a layered structure, the fibrous matrix may comprise two different webs, optionally both prebonded, which optionally exhibit a different pore size or composition.

The SAP particles may then be arranged at different concentrations optionally segregated in particles size.

The absorbent structure may also have gradients of concentrations of the materials. Thus, the fibrous matrix may exhibit a pore size gradient, and the SAP particles may have a corresponding concentration profile.

The absorbent structure may further comprise combinations of the above. The SAP particles may be arranged in separate layers, e.g. one oriented from a first fibrous matrix towards the cover web, and another one oriented from a first or a second fibrous matrix towards the carrier web.

It is important for the present invention that there is sufficient meltfusionable material present to allow meltfusion bonding. The term "sufficient" refers to either sufficient meltfusionable material allowing bonding regions of this material being formed. The term "sufficient" may also describe the situation that the meltfusionable material connects fibres of unmolten material to each other or to other meltfusionable or not melt fusionable material.

Thus it is preferred to have at least 5% of meltfusionable material, often more than 10% in the absorbent structure.

The skilled person will readily realize that the meltfusionable material and the fibrous structure may be unitary, and then all weight percentages apply to the unitary matrix providing meltfusion and fibrous material.

However, in order not to overly compromise the absorbency performance of the material, the amount of meltfusionable material should not exceed 50%, preferably not 40% of the absorbent structure.

Correspondingly, there should be sufficient amount of fibrous material available to form a fibrous matrix allowing SAP particles to be positioned therein.

Further, there should be sufficient amount of SAP particles in the structure to ensure good absorbency, and the absorbent structure may comprise more than 60%, preferably more than 70%, often more than 80% or even more than 90% of SAP.

Also, the local basis weight of the SAP particles should be sufficiently high so as to allow repositioning of the SAP particles upon swelling. As will be discussed herein below, this would not be satisfied, if—for example—less than a monolayer of materials would be introduced, as these would only swell to about three or four times their z-directional thickness and not de-bond the bond points. Once having more than a monolayer of swollen material, the swelling will reposition the particles in the fibrous matrix predominantly z-directionally, thusly increasing the thickness over proportionally and thusly easing the de-bonding.

The particles should be arranged exhibiting more than a "monolayer" structure, and preferably form multi-layer structure as may be expressed in terms of number of overlaying particle layers, or may be expressed by a local or an averaged basis weight, referring to the weight of particles for a given unit area. The skilled person will readily realize, that even a "local" basis weight will need a certain amount of averaging, which should be made over an area of 25 mm$^2$. When the basis weight in a given area is by design not constant over this region, the basis weight distribution may be approximated by a smoothed curve over several local determinations. Both local and average basis weights for the SAP particle should not be less than about 50 g/m$^2$, preferably be more than 50 g/m$^2$, typically be more than about 150 g/m$^2$, though often also more than 400 g/m$^2$ or even beyond 800 g/m$^2$. Preferably, the basis weights should not be more than about 2000 g/m$^2$.

The absorbent structure may have in the x-y-extension homogeneous composition and properties or it may form regions with varying composition or properties. These regions may have sharp limits or the transition may be gradual. For example it can be contemplated, that an absorbent structure is part of an absorbent article and may have different absorbency properties in one region as compared to another, such as when less absorbent capacity is positioned in the waist regions of a diaper than compared to the crotch region. Also, when such absorbent structures are formed on a manufacturing line, subsequent regions with high absorbency for forming the absorbent core of the articles may be separated in machine direction by regions with very low or even essentially no absorbent capacity. Thus, an absorbent structure may comprise sub-regions, or several structures may form macro-structures.

The absorbent structure according to the present invention further comprises meltfusion bonds, i.e. it comprises bonding of the fibres of the fibrous matrix by molten material. It is a particular feature of the present invention that the meltfusion is executed in discrete bond or bonding regions, also interchangingly referred to as bond points. In the bond regions, the meltfusionable material is molten or at least sufficiently softened so as to allow plastic deformation. In this bond region, the fibrous matrix material is compressed so as to exhibit a smaller calliper or thickness than the surrounding region. Around a centre region of the bond region, where this plastic deformation and reduction of calliper or thickness occurred, the bond region may comprise a transition region, as a transition from the centre region to the surrounding region of the fibrous matrix which is not being consolidated the same way as the bond region. In this transition region, the thickness/calliper of the web increases from the centre region to the surrounding region, whilst the local density decreases accordingly. Some of the molten or plastically deformed material may be squeezed from the central region into the transition region.

The bond region exhibits a certain geometric extension, both with regard to the x-y-dimensions of the web, as could be seen in a x-y-top view of the web and to the z-directional dimension, as can for example be seen in a cross-sectional cut along the thickness direction of the web.

Preferably, the bond regions exhibit x-y-directionally an elongated shape with an aspect ratio of their long axis to their short axis of at least 1.05 to 1, preferably of 1.1 to 1, and even up to 200:1. Preferably, the shape is elliptical, more preferably non-circular in the top view. Also in an x-z- or y-z-oriented cross-section through a bond point the bond point may exhibit at least partially elliptically shaped boundaries. The major or longer axis of the ellipse may be aligned with any major direction of the web, though in a particular embodiment the axis may be at an angle of more than 0° and less than 45° to the machine directional axis of a web. Whilst geometrically strictly speaking also circles represent a special form of an ellipse, they are less preferred.

Several bond regions form one or several readily recognizable repeating pattern(s). Therein a row of regions is a group of regions that are arranged predominantly along the cross-direction, whilst in a column the group of regions is arranged predominantly along the machine direction. Within the present description, "predominantly" refers to the situation, that the projection of a characteristic line onto one direction is larger than onto the other direction perpendicular thereto. There may be more than one pattern simultaneously in one web, which may be intermittent, overlaying, interdigitizing. Such patterns may be formed simultaneously, and then are typically in a specific registry to each other. Such patterns may also be formed independently of each other and then often have no direct correlation to each other, such as when a web already having a pre-bonding pattern of any kind is submitted to a process according to the present invention, or if a web is treated twice in subsequent process steps according to the present invention. Such pattern may also comprise sub-patterns and or may be part of a macro-pattern.

The absorbent structure may exhibit a pattern over its entirety. Alternatively, the absorbent structure may comprise two or more patterns over its entirety. Further, the absorbent structure may exhibit sub-pattern or a pattern which may be a sub pattern to a macro-pattern.

A bond point may be used for bonding or consolidating components of fibrous matrix. Also, bonding may be performed between strata or layers of one or more fibrous matrices, such as when spun-laid or melt blown layers are positioned on each other or on a layer of carded staple fibres, bonding can be achieved across all or some of these layers or strata. Similarly, bonding may be achieved between two or more webs, which may differ in at least one property, such as a film and a fibrous matrix. Further, the process according to the present invention may create an aperture in one of the layers but a bond point in one or preferably two enveloping fibrous matrices.

In particular for the bonding of a fibrous matrix, the preferred bonding process according to the present invention provides structures exhibiting improved tactile softness. Without wishing to be bound by the theory, it is believed, that this improvement results from the gradual transition of a fibrous structure around the bond regions to the molten centre of the regions.

The present invention allows to create very specific bonding patterns by modifying one or more of the following parameters of the bonding pattern
 size and shape of bonding points, i.e. length, width and aspect ratio;
 length/width distance, which may be uniform or not;
 angle of pattern lines;
 angle of bond indentation;
 size and aspect ratio of bonding indentation;

It should be noted that fewer but larger bonding points can result in the same overall bonding respective de-bonding force, but may result in more pronounced quilting in the dry state or during swelling. For absorbent articles being worn on the lower torso, such as disposable absorbent articles like diapers, such a strong quilting may further have negative impact on perception of the wearer and on the fit of the article.

The area of individual bonding points is preferably less than less than about 30 $mm^2$, but more than 0.1 $mm^2$. If a bonding point comprises sub-regions, these numbers refer to the area circumscribing these subregions.

The skilled person will readily realize that the selection of the bond point size will depend also on the thickness and amount of fibres, i.e. when less and larger fibres are employed, the bond points will preferably be larger, whilst for finer and more fibres the bond points can also be smaller.

Preferably, the bonding points exhibit an aspect ratio of their long axis to their short axis of at least 1.05 to 1, preferably of 1.1 to 1, and even up to 200:1. In a preferred embodiment, the long axis of the bonding points is positioned such that its smallest angle to the pattern line is an angle of less than 90°. In case of a curvilinear pattern line, the angle is determined versus a tangent of the pattern line in the bonding point centre.

The distance of the bonding points along the pattern line may be less than about half a millimeter or more than 50 mm, depending on the desired degree of barrier function of the bonding pattern and/or the immobilization function with regard to the free flowing material.

The number of bonding points per area may be between one bonding point per each 9 $cm^2$ to one bonding point per each 9 $mm^2$.

Within the present invention, the bonding points may be formed by conventional means, such as adhesive application or meltfusion bonding. A particular execution is achieved by heat- or melt-fusing the webs together.

To this end, the webs are guided through a gap formed by a pair of anvils whilst or after the temperature of at least one, often of both of the webs is or has been raised by an energy source to the softening, often the melt temperature of the meltfusionable compound. Upon application of at least some pressure the softened or molten compounds form the bonding points.

Energy sources may be alone or in combination:
 pre-heated web material;
 the pressurizing as such by a pair of rolls acting under high pressure;
 heated (often patterned) bonding roll(s);
 non-contact or indirect heating, such as by hot-air blowing or radiation heating;
 a preferred execution is sonic, more preferably ultrasonic energy emitted by a "sonotrode", optionally a rotating sonotrode, such as described in US20050034820 (Herrmann Ultraschall, Schneider).

Typically, the pair of anvils is made of an energy source and a counter acting anvil, though the distinction between "energy source" and "anvil" may in some instances be blurred, such as when two non-heated anvils are forming the gap and the energy has already been transferred to the web(s) or is induced by pressing the anvils together. Similarly, the term "counteracting" should not be seen limiting, but rather also to encompass the situation of the energy source being the first anvil and essentially stationary and the second "counteracting" anvil being moveable.

Within the present invention and as will be discussed in more detail, the "second" one of the anvils is the support system for the fibrous matrix and this is considered as the "counteracting" anvil. Typically, the opposed "first" anvil is the energy source, whilst at least some of the energy may also come through the first web support system, or from another energy source.

A particular execution of the present invention employs bonding by using an ultrasonic bonding process employing a flexible anvil, such as described in co-pending patent publication WO2012/041055 (C4S, Schmitz). A particular execution of the present invention employs bonding pattern as described in co-pending application GB1216670 (C4S, Schmitz, unpublished). To both of these applications express reference is made.

In order to provide good liquid absorbency, the absorbent structure according to the present invention should not restrict the swelling of the SAP particles unduly.

This is achieved by designing the meltfusion bonding such that it exhibits a predetermined bond strength that is sufficiently high to withstand manufacturing, transport, pre-wetting, and in-use mechanical stress whilst being sufficiently low to de-bond upon swelling of the SAP particles.

The meltfusion bonding system is configured to de-bond at an applied load which is less than a load which would induce destructively tearing of the material.

It should be noted that there are several means to adjust the bond strength:
1) The amount of meltfusionable material as absolute amount respectively basis weight and relative to fibres and to SAP particles;
2) The bonding temperature relative to melt/softening point of meltfusionable material;
3) The bonding pattern, i.e. bonding point size/shape and the bonding point pattern (points per area unit; orientation, etc.);
4) The bonding pressure resp. force;
5) In particular when using z-directional gradient structures, the bonding point may have a z-directional strength profile, e.g. the bonding may not reach z-directionally completely through the structure but may only meltfusion bond certain regions.

Whilst it is believed that when employing the particular bonding mechanism with flexible, such as helical anvils, this will per se result in bonding regions that are essentially free of particulate SAP, small amounts thereof may be present in the bonding regions. This is less preferred because the bond strength may exhibit a greater variability from one point to the next, but also as the tight fixation of the SAP particle in the bond point might reduce its absorbency.

As will be discussed in more detail herein below, it is believed that bonding or adhesion between the SAP particles and the fibrous matrix limits the repositioning. It is further believed, that it is advantageous to allow repositioning of the fibres of the fibrous matrix relative to each other respectively to the SAP particles.

As has been described in the above, the meltfusion bonding compresses the fibrous matrix with SAP particles embedded therein to form the bonding regions. Henceforth, the material density in the bonding regions is increased, possibly up to the polymer density of the materials, i.e. the material is completely compressed and solidified. Optionally, there are still some fibre matrix pores in the bond regions, but at a much smaller pore size as compared to prior to the bonding.

However, depending on the distance between the bonding regions, the fibrous matrix between two respectively directly neighbouring bonding points may remain essentially uncompressed or may be compressed somewhat, but to a lesser degree than in the bonding regions. In either case, the result is a x-y-directional pore size gradient—smaller or essentially non-existing at the bond points, and larger between the points, optionally gradually increasing with distance to the bonding regions. Such structures may then exhibit a quilt-like form.

This is further explained by referring to FIG. 1. FIG. 1A schematically depicts a fibrous matrix 110 with fibres 120 and pores 130 between these fibres. FIG. 1B further shows dry SAP particles 140 embedded in the pores. A bonding region 200 is indicated wherein the pore size appears reduced. The structure exhibits a z-directional thickness 150 and a certain x- or y-directional extension is indicated by line 160.

In FIG. 1C the structure is schematically represented after wetting and respective swelling. As the structure swells predominantly z-directionally, as indicated by significantly increased thickness 150' and the fibres reposition as well as the swollen particles 140', which also swell into the de-bonded regions 200'. As indicated, there is only a slight change in the respective x- or y-directional extension 160'. It is further contemplated that the structure may further be compressed reversibly or at least not non-reversibly after being bonded. This may be achieved by compressing the structure between smooth or patterned calender rolls at a temperature sufficiently low to not allow melting or plastic deformation of the materials, such as when compressing the structure in order to achieve lower thickness when combining the structure into an article, such as—without intending any limitation—a diaper. In particular in such a case, the use of resilient fibres is preferred.

Considering the finished bonded absorbent structure, it may be difficult to assess the pore sizes of the fibrous matrix other than by optical analysis, but a skilled person will readily realize that SAP particles are embedded in the pores of a fibrous matrix.

Considering, that SAP particles typically absorb 20- to over 30-times their own weight of liquid to form a gel, the volume of such particles will increase in the order of magnitude of the cube root of their capacity, if for a first approximation the shape will be assumed to be spherical. Henceforth it is preferred, that the maximum pore size is larger than the maximum particle size of the SAP particles. Accordingly, the median pore size is preferably larger than the median particle size of the dry SAP particles.

Optionally, the porous structure may have a z-directional pore size gradient, such that larger particles may be restrained in zones with larger pores and smaller particles in zones with smaller pores.

Thus, the absorbent structure according to the present invention may be an essentially homogeneous web in x- and y-direction. The absorbent structure may also be in the form of a macro-pattern, such as formed by sub-patterns extending in the x- and y-direction. Without intending any limitation, such sub-structure may correspond to an absorbent core or an absorbent article, and the absorbent structure may be a repeating series of such sub-structures.

The absorbent structure may exhibit a quilted form, whereby the structure shows indentations corresponding to the bonding points whilst the fibrous structure between the bonding points forms pillow like structures.

An absorbent structure according to the present invention may comprise further elements. For example, the structure may comprise more than the one cover sheet, for example one on each of the x-y-directionally extending surfaces.

Such additional cover sheets may also serve to retain parts of the absorbent structure in a wet state and after the meltfusion bonds are released and thus function as a secondary containment means in addition to the primary ones of containing the SAP particles in the meltfusion bonded fibrous matrix. The structure may further comprise liquid handling enhancement means, as may provide preferential x- and/or y-directional liquid distribution, or an interim liquid storage capability that enables to receive liquid such as upon a urine gush, but also to release this liquid to the SAP so as to provide surge capacity for a subsequent liquid gush.

The absorbent structure or its sub-structures may have further secondary containment means, such circumferentially extending intermittent or continuous bonding, which may exhibit a bond strength higher than the one of the bond points in the structure. This may also result in confining the absorbent structure in its x- and y-directional expansion upon wetting.

Further, in addition to the meltfusion bonds which allow expansion upon de-bonding and thusly function as primary expansion aids, the absorbent structure may have secondary expansion aids to allow retaining of the materials of the absorbent structure without restraining the swelling of the SAP. Such secondary expansion aids may be circumferential folds with intermittent or continuous bonds, that may de-bond upon a certain expansion pressure of the absorbent structure, in analogy to the meltfusion bonds, or which may de-bond by mere wetting, in analogy to the mechanisms as described in U.S. Pat. No. 5,411,497 (K C, Tanzer). Such an expansion aid may also be a tear-line in an enveloping sheet, e.g. an intermittent "perf'n pop" or "pop-open" cut line.

Prior to the wetting, the fibrous matrix bonded by the meltfusion bond points serves as the primary containment means by immobilizing the dry unswollen SAP particles within pores of the fibrous structure.

The arrangement of the bond points being arranged in a particular and predetermined pattern and being surrounded by unbonded regions will provide a quilted structure, wherein the bond points form depressions and the unbonded regions pillow-like elevations.

A secondary dry containment means may be provided in the form of an additional layer of web material, such as a cover web. Optionally such an additional layer may follow the quilted structure, or may lay flat over it, i.e. touching the bonded matrix at the elevated regions whilst bridging the bond point depressions.

This quilting also provides a further density gradient in the structure, which is believed to further enhance the good liquid distribution properties of the structure. The embedding of the SAP particles in the fibrous matrix provides a structure exhibiting a good touch, for examples softer as compared to sandwiched SAP pocket structures.

Upon wetting of the absorbent structure the SAP particles will start swelling. As the absorption speed of SAP is relatively slow, liquid still can be distributed through pores of the fibrous matrix that are essentially free of SAP particles but also through void spaces between the fibres and the particles, further aided by the pore size gradient resulting from the quilting effect around the bond points.

It is believed that this is beneficial for an overall liquid handling performance, as the absorbent structure will not be loaded only locally, but over a larger area. Therefore it may be a particular advantage that the bonding regions will only de-bond upon the swelling of the SAP but not already upon first contact with the wetting liquid.

Upon swelling of the particles and as it is preferred that the fibrous matrix is not too tightly pre-bonded, the particles as well as the fibres of the fibrous matrix will rearrange their position relative to each other.

With an increased amount of imbibed liquid, the particles will swell, increase in size and build up a swelling force respectively an expansion pressure. Within the present context, the term "swelling force" is the capability of a SAP particle to exert a force against a restraining counter force upon swelling. As superabsorbent polymers typically swell isotropically, also the swelling force will be omni-directional, i.e. have force components or vectors in all three Cartesian directions. Without wishing to be bound by the theory, it is believed that this swelling force correlates to the ability to absorb liquid under pressure, which may be assessed by determining the absorption under pressure as described in the test method section.

When several SAP particles are arranged in a close relative position to each other, the particles may restrain the swelling of neighbouring particles. For explanatory purposes a monolayer of unswollen i.e. dry SAP particles positioned in a touching relationship on a flat surface is considered. Upon swelling of the particles, the interparticle voids may be filled by the swollen gel. Upon further swelling by provision of further liquid, the particles may stop swelling in particular for SAP of low gel strength, absorbency under pressure, or Saline flow conductivity (SFC). However, modern SAP particles exhibiting higher gel strength, absorbency under pressure and SFC values will continue to swell, and the swelling forces will result in repositioning of the particles. As—in this thought experiment—the repositioning is restricted by the support surface, it may only happen x-y-directionally or z-directionally upwardly. x-y-directionally the repositioning is restricted by the friction of the particles to the support, and in the z-direction the particles have to overcome gravity. As a consequence, such a monolayer of dry particles will typically result in "stacking" of several particles z-directionally, in particular when the x-y-directional expansion is hindered. or which may also be induced by circumferentially positioned containment means limiting the x-y-directional expansion.

Consequently such a particle accumulation will expand preferentially, if not predominantly or even exclusively z-directionally. The ability to create a z-directional force can be determined by positioning particles in a circumferentially confined space, allow the swelling by providing liquid, such a 0.9% saline solution, and monitoring the swelling pressure that the particles may exert against a lid positioned on top of them.

This ability to exert a force is also important in the present context for the de-bonding of the meltfusion bonds. The mechanism is very similar to the one described in the above. When dry, the particles may be separated by fibres of the fibrous matrix, or may be in direct contact with neighbouring particles. Upon initial swelling, the spaces between particles and/or fibres are filled. Upon provision of further fluid, the neighbouring particles are a hindrance for further swelling. The structure exhibits a relatively large x-y-extension and exhibits due to the bonding point pattern a relatively high resistance to x-y-directional repositioning. However, due to the much smaller y-directional extension and the repositionability of the fibres, z-directional repositioning of the swelling particles is less restrained—at least in regions sufficiently distant from bonding points, as in the proximity of these the meltfusion bonding also restricts the z-directional expansion. However, because of the at least preferential expansion in the z-direction, the isotropic swelling force of the SAP particles will be re-directed into a z-directional expansion force. This force is now transmitted via the fibrous structure, optionally supported by carrier or cover webs, to the bonding points and creates a pull force at each of the points. As a skilled person will realize, this pull force acts in an abutting mode on the bonding point, which results in less strength of the bond as compared to an overlap mode, which is the predominant force transmission mode for a dry structure, where typically higher forces are transmitted along the x-y-direction.

Upon this expansion force, the meltfusion bonds can de-bond one after the next depending on the availability of the liquid. If the meltfusion bond strength is not homogeneously executed in the z-direction, such a bonding point may give consecutively in the z-direction, depending on the direction from where the liquid is provided.

Upon sufficient wetting, the SAP particles swell and because of the particular execution of the bonding points de-bond the bonds. The particles are now immobilized by the fibres of the fibrous matrix as the primary wet containment means.

Thus, the fibrous matrix provides a dual functionality of both dry and wet immobilization of SAP particles. It also functions as secondary wet containment means, and it may further enhance the integrity of the structure. Such secondary containment means may function z-directionally, such as cover webs, or laterally, such as connection lines positioned outwardly of SAP particle loaded regions of the structures. Thus, the absorbent structure may be regioned or have a certain limited x- and/or y-directional extension, in which the SAP particles are deposited and where the meltfusion bonding points form a pattern. x- and/or—y-directionally positioned or circumscribing connecting lines or regions are formed such as connecting cover or carrier webs extending from the primary absorbent structure outwardly.

Preferably, the circumscribing connecting is positioned and/or executed such that it does not limit the swelling of the SAP particles. To this end, the connecting may be positioned sufficiently away from the particle containing and swelling regions whilst the region between the connecting and the swelling regions is essentially unconnected, or only weakly connected, or in a way that de-bonds upon wetting. Optionally, the absorbent structure may comprise one or more cover or carrier web(s) connected to the x-y-extending surface of the outside of the structure, which may comprise expansion aids, such as a fold or a pop-open tear line, which may be activated upon wetting or upon exertion of a swelling force.

If the connecting region is positioned close to the swelling regions, it may comprise a expansion aid, such as an unconnected, only weakly or wetting releasably connected fold, for example a Z-fold, which extends z-directionally upon the swelling of the SAP.

Absorbent structures according to the present invention may be employed in a wide range of articles and products, such as meat pads, bed pads and the like, or as a preferred application in absorbent articles, such as baby or adult incontinence articles, feminine hygiene articles and the like. In particular when producing absorbent structures for the latter applications it may be desirable to have a region of the absorbent structure that corresponds to an absorbent core of an absorbent article which corresponds to the meltfusion bonding pattern described herein. Considering a continuous manufacturing process, a series of such absorbent structures may form a macro pattern or regions of subsequent patterns or regions. The absorbent structure may optionally comprise sub-patterns, or differently patterned regions, for example regions corresponding to the crotch region of a wearer during use being differently patterned and optionally comprise different compositions or properties.

The articles may further comprise elements as usually employed in such articles, such as
- further liquid handling elements, as may be provided separately to or integral with elements already described, i.e. the porous matrix for receiving the SAP particles, and/or the carrier or cover webs, as applicable;
- liquid retention means such as liquid impermeable layers;
- chassis elements for allowing fixation of said article on a wearer.

In a second aspect the present invention is a method for manufacturing absorbent structures comprising a fibrous matrix and SAP particles embedded therein, which is bonded by meltfusion bond points. The process comprises the steps of providing a fibrous matrix, meltfusionable material and SAP particles. The SAP particles are positioned within the interfibre pores of the fibre matrix. Upon creating meltfusion bonds of a predetermined bond strength, a bonded absorbent structure is formed.

A suitable fibrous matrix has been described in general terms in the sections hereinabove. Thus such a fibrous matrix may be provided as one or more pre-formed, optionally pre-bonded web(s) supplied to the process before performing the meltfusion bonding.

Alternatively, such a fibrous matrix can be formed essentially in-line, i.e. in a continuous process with the forming of the unbonded structure loaded with SAP particles whilst or after the forming of the fibrous matrix and the meltfusion bonding thereof. Optionally such a formed fibrous matrix can exhibit an essentially homogeneous pore size distribution or may comprise z- and/or x-, y-directionally arranged distinct or gradually changing pore size distributions. The fibrous matrix may also be provided by combining one or more of each of the above alternatives, such as by providing a pre-formed and pre-bonded web and accumulating in-line further fibres to form a composite fibrous matrix.

The means and the ways to create such fibrous matrix are generally not critical for the present invention and are well known in the art. Optionally, the fibrous matrix may be further modified during the process according to the present invention as will be discussed in more detail herein below.

The SAP particles may be provided by conventional means and may be metered continuously at a constant or predeterminedly changing feed rate or intermittently, as well known in the art.

As described hereinabove, the meltfusionable material may be integral with the fibrous material. In addition thereto or alternatively the meltfusionable material may be provided separately, such as by adding meltfusionable material to the fibrous matrix. In a particular execution, though often less preferred execution, the meltfusionable material may be in granular form added to the fibrous matrix analogously to the addition of the SAP particles or even mixed with the SAP particles. In another particular execution the meltfusionable material is provided as one or more web materials as may be positioned on the surface of the absorbent structure or which may comprise fibres of the fibrous matrix on both sides of the web of the meltfusionable material.

The SAP particles may be added in a single step, or there may be several steps providing SAP particles at various stages of the process.

For the present invention it is not critical how the particles are integrated into the fibrous structure. In a particular execution, the particles are supplied by gravity and/or a forced air flow to a pre-formed fibrous structure. Additionally or alternatively the particles can be supplied by gravity and/or a forced air flow whilst the fibrous matrix is formed.

The positioning of the SAP particles in the pores of the fibrous matrix may be aided by applying air flow, such as air suction z-directionally through the fibrous matrix. Optionally such an air flow may be x-y-directionally homogeneous, or may be adapted to match x-y-directional pattern of the bonding regions and/or of substructures. Additionally or alternatively the positioning may be aided by applying other mechanical energy, such as tapping, shaking or the like.

The particles may be provided to the fibrous structure whilst or shortly after the pore size of the fibrous matrix has been modified as described herein below. Preferably, the relation of the pore size respectively interfibrous voids to the size of the SAP is such that in a dry state the SAP readily fits into and even can readily penetrate into the voids, but also such that the swollen SAP is restrained by the porous structure.

This is explained by referring to FIG. 2. It depicts schematically and not to scale the particle size distribution of particulate SAP, shown by the solid line curve 1100 of relative amount 1110 of particles (see left axis) exhibiting a certain diameter, see size 1000. The skilled reader will realize that the area under the curve should sum up to 100%, and also that such a smooth curve 1100 is often determined by sieving into certain fractions. Also both tails of the particle size distribution may be "cut off", such as for processing reasons, such that the particle size distribution shows a clear minimum (1010) and maximum (1020) value.

The diagram further shows—also schematically and not to scale—a pore size distribution of a fibrous matrix, The dashed line 1200 shows for certain pore diameters or sizes 1000 the relative frequency 1210. As for the particles, the area under the curve should sum up to 100%. For the pore size, the tail may extend towards very small pores, here indicated by the cut off 1210 at the left axis. The matrix exhibits a maximum pore size 1220. It should be noted that for the present explanation the term "pore size" refers to matrix of fibres only, i.e. there are no SAP particles considered.

In order to function according to the present invention, SAP particles need to penetrate into the pores of the fibrous matrix. If there are sufficiently large pores, the particles may be embedded, if not, some of the particles will remain on the surface of the fibrous matrix. If a large particle is positioned on a pore region exhibiting too small pores for penetrating into, the particle may be moved into neighbouring larger pores, such as by tapping or air blowing or sucking or other embedding aids. If the particles are relatively too small, they might penetrate through the fibrous structure and—if present—be caught by an additional carrier. Also, even for an even pore size distribution smaller particles can be caught by relatively larger pores in analogy to the depth filtering mechanism.

The skilled person will readily realize that the ability of the fibrous matrix to retain SAP particles will not only depend on the pore size distribution. For example, even if there is a small frequency of small pores, an increase of the thickness of the web, i.e. of the basis weight, will increase the ability of the structure to accommodate a given amount of small particles.

Referring again to FIG. 2, the dash-dotted line 1300 depicts the pore size distribution of a fibrous matrix exhibiting relatively small pores. In order to increase the ability to retain relatively large amounts of larger particles, the pore size of such a fibrous matrix may be shifted to larger values, such as to a curve 1200, by submitting the fibrous matrix to process steps that temporarily or permanently change the pore size respectively the pore size distribution, such as by tentering (i.e. x- and/or y-directional stretching of the structure), or mechanical activation, such as by submitting the web to an incremental stretching between two flat, profiled or intermeshing profiled rolls, such as described in general terms in WO2007/107846. The method described therein involves providing fibrous web materials and providing a pair of rolls to form a nip through which the absorbent fibrous web materials are processed, where the rolls are selected from processes consisting of ring rolling, SELF, micro-SELF and aperturing of rotary knife. The absorbent fibrous web materials are deformed by processing through the rolls. For the present application such a process may be modified by activating a single fibrous matrix, which may already been loaded with SAP particles, which may—due to insufficient amount of large enough pores—not have penetrated into the pores prior to activating. After releasing the modifying forces, the fibrous matrix may maintain the increased pore sizes, or at least some of the pores may return to smaller pores. If SAP particles were in such pores reducing their size again, these would be captured even more strongly in their position.

Optionally, a further web material having a prescribed pore size may be positioned on the surface of the fibrous structure, thereby preventing particles to leave the fibrous structure. Particularly suited materials for this may comprise meltblown webs.

It should be noted that the combining of the various steps of adding the SAP particles and applying air flow, mechanical aids, or vacuum influence the distribution of the particles in the fibrous matrix. For example, if a vacuum is applied to a fibrous matrix, this may impact the pore size of the matrix. Accordingly, the particle deposition and distribution may be influenced by the vacuum not only by the suction effect on the particles but also by the suction effect on the fibrous matrix.

It is an important aspect of the present invention that discrete meltfusion bond points are formed, preferably of the shape and in pattern as described hereinabove.

To this end, the fibrous matrix, optionally combined with a further web, is guided through a gap formed by a pair of anvils whilst or after the temperature is or has been raised by an energy source to the softening, often the melt temperature of the meltfusionable material of the fibrous matrix or of the further web. Upon application of at least some pressure the softened or molten compounds form the bonding points.

Energy sources may be alone or in combination:
pre-heated fibrous matrix material;
the pressurizing as such by a pair of rolls acting under high pressure;
heated (often patterned) bonding roll(s);
non-contact or indirect heating, such as by hot-air blowing or radiation heating;

A particularly preferred execution for the energy source is sonic, more preferably ultrasonic energy emitted by a "sonotrode", optionally a rotating sonotrode, such as described in US20050034820 and commercially available such as from Herrmann Ultraschall GmbH, Germany.

Most preferably one of the anvils is a flexible support structure for supporting the fibrous matrix which is considered as counteracting anvils cooperating with the sonotrode. The principles of such a process are described in the above mentioned applications WO2012/042055 (C4S, Schmitz)

and GB1216670 (C4S, Schmitz, unpublished), which are expressly incorporated herein by reference.

When the sonotrode contacts the fibrous matrix, it compresses the matrix into the space between the most upwardly positioned support points, at which the meltfusioning takes place. Thus in the particularly preferred execution of a support structure being executes as helical springs, the fibrous matrix is gently pressed between the upwardly (i.e. towards the sonotrode) positioned parts of the helical spring, where elliptical melt fusion bonding points are formed. Between the patterned arrangement of the bonding points, the fibrous matrix is only slightly and typically reversibly deformed, unless specific means are implemented such as additional support member between the helical springs that can provide a desired moderate compaction also outside of the bonding points.

The particular execution with the flexible anvils is believed to provide a further advantage in that it allows creating essentially particle free bonding regions even if the SAP particles are applied evenly across the x-y-direction. Without wishing to be bound by the explanation, the shape of the anvil structure exhibiting essentially no flat surface but rather a surface sloping away in all directions allows the SAP particles located in the bonding regions to dislocate slightly just prior to the bonding outside of the bonding regions.

The forming of the meltfusion bond region is creating regions of varying densities around the bonding regions. Whilst no strong compression between the heat source, such as the sonotrode and the anvil elements is deemed to be necessary, the melting of the meltfusionable material will inevitably increase the local density of the materials in the bonding region, and—as the local basis weight per unit area remains essentially constant—reduce the calliper of the structure in the bonding points.

In order to explain even further how the process according to the present invention may be configured, reference is made to schematic FIGS. 3 A to D showing exemplarily such process set ups. These should, however not be seen in any way limiting with regard to other arrangements and executions.

Figure 3A:
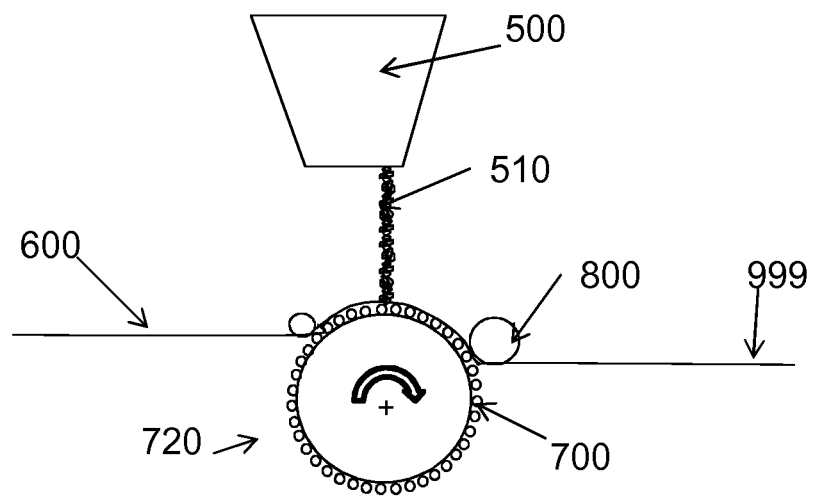
FIG. 3A to D depict schematically process set-ups as may be suitably used according to the process aspects of the present invention.

FIG. 3A depicts a SAP particle supply 500, such as conventional hopper with a dosing unit (not shown). Particulate SAP falls in a stream 510 onto a fibrous matrix, here shown as a pre-bonded web, as may be a high-loft material described herein above, that is supported by a support structure, here shown as helical anvil system on a rotating drum 720. The fibrous matrix with the SAP particles are fed towards a gap between the anvil and a heat source, here shown as rotating sonotrode 800 of a ultrasonic welding system to form the meltfusion bonded absorbent structure 999.

Figure 3B:
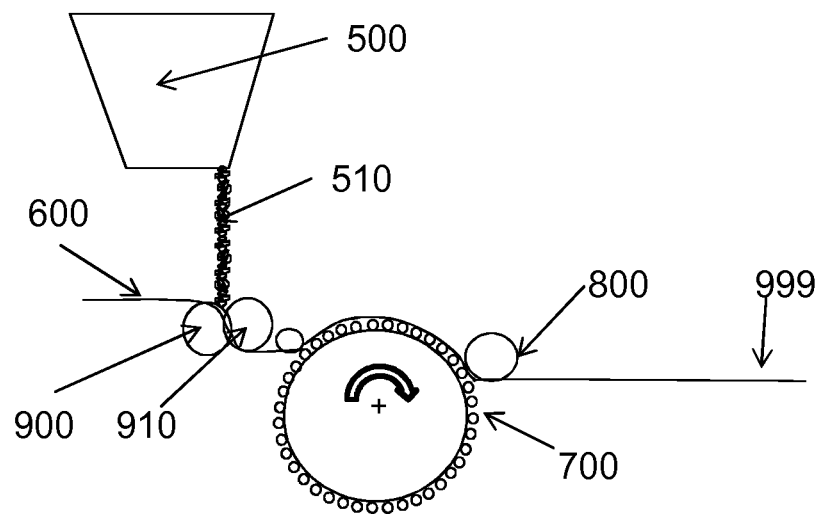

FIG. 3B depicts a similar system, wherein the fibrous structure loaded with SAP particles is fed into a gap between two interdigitizing mechanical activation rolls 900 and 910 for modifying the pore size distribution of the fibrous structure. Thereafter, the fibrous matrix is bonded as described in the context of FIG. 3A to form the absorbent structure 999.

Figure 3C:
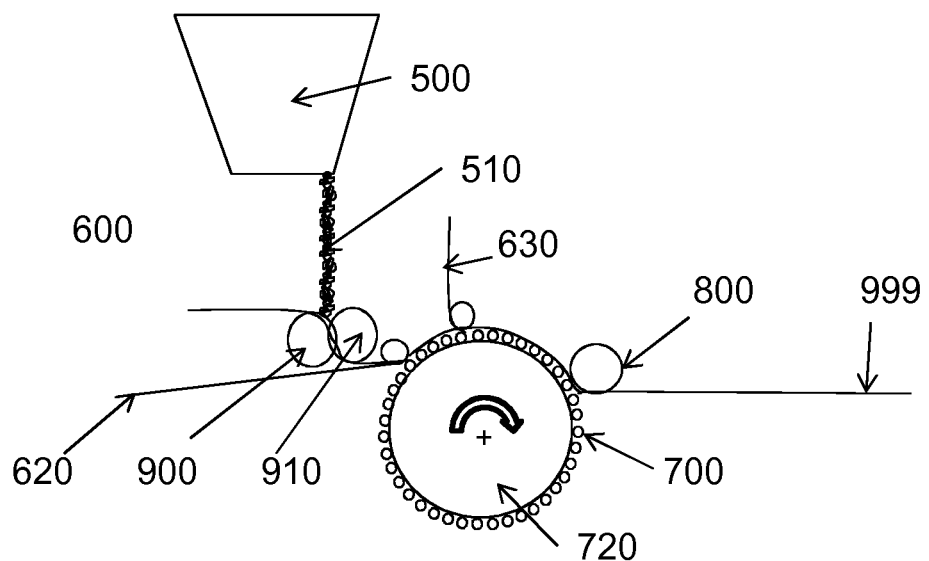
Figure 3D:
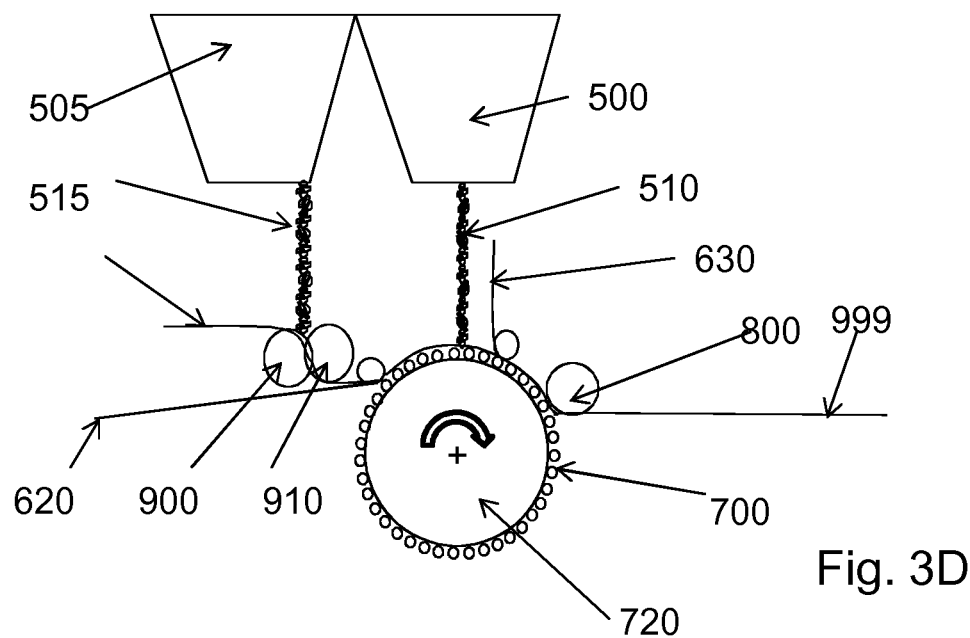

FIG. 3C depicts a similar system as shown in FIG. 3B, now with additional web materials, such as carrier web 620 and a cover web 630 enveloping the fibrous matrix before all three are meltfusion bonded to form the absorbent structure 999.

FIG. 3C depicts a further combination of process elements, here showing two SAP particles supply systems, which may provide essentially the same or different types SAP particles, A first stream of particles 510 is fed as shown in FIG. 3B to the fibrous web 600 just prior to the mechanical activation between interdigitizing rolls 900 and 910, whilst a second stream of particles 515 is fed towards rotating drum 720 with the support structure, here a helical anvil 700 prior to bonding with sonotrode 800 to form the absorbent structure 999.

In a particular execution, the particle stream 510 may be modulated so as to provide a varying distribution of particles upon lay down. This modulation may be by any means resulting in a variation across the y-direction and/or the x-direction. In particular the latter may be achieved by interrupting the particle stream, such as by blowing or sucking air and thus removing the particles from the stream for a predetermined time. A very convenient and simple construction employs a vacuum cylinder rotating around its axis which is positioned between the SAP metering device and the rotating drum 720 in the proximity of the particle stream and oriented along the y-direction. The cylinder further comprises a slit of a predetermined width, such that when the slit is oriented towards the particle stream, the particles are sucked into the cylinder, from where they may be recycled to the SAP particle supply system, but alternatively they may be fed towards the rotating drum on which already a carrier material is positioned, such that in such a predetermined region an increase of SAP basis weight can be realized.

EXAMPLES

A comparative example has been constructed according to the teaching of co-pending application GB1216670.

One layer of conventional topsheet, a 19 $g/m^2$ hydrophilic spunbonded polypropylene nonwoven material, has been cut to 20 cm by 20 cm and placed on a set of intermeshed helical springs, having a circular wire diameter of 1.5 mm, an outer spring diameter of 1 cm and a pitch of 1.7 cm, covering an area of about 20 cm 20 cm. A cardboard mask with a square opening of 10 cm by 10 cm was placed thereon and slight vacuum was applied from underneath the support board for the set of helical springs to ease flat positioning of the topsheet layer and create slight indentations or pockets between the uppermost support points.

4 g of conventional SAP particles of the Type EK-X EN67, available from EKTOTEC GmbH, Haan, Germany, have been manually sprinkled over the mask area of 10 cm by 10 cm. In spite of even application over the area, the pockets were filled more than the regions around the support points.

A second topsheet layer of 20 cm by 20 cm was positioned over the first and the SAP particles, thusly forming a sandwich structure.

By means of a manually operated ultrasonic sonotrode as available from Sonic Italy, Rho, Milan, Italy, with approximately 20 kHz frequency and a circular sonotrode head of 6 mm, the two webs were meltfusion bonded at the uppermost support points of the helical springs, thereby creating elliptical bonding points of approximately 1.5 mm length and about 0.5 mm width.

A second ultrasonic bond line was made circumferentially outwardly of the sandwich region, forming a 15 cm by 15 cm square.

A second sample was constructed according to the teaching of the present invention.

One layer of conventional topsheet, a 19 $g/m^2$ hydrophilic spunbonded polypropylene nonwoven material, has been cut to about 20 cm by 20 cm and placed on a set of intermeshed parallel helical springs, having a circular wire diameter of 1 mm, an outer spring diameter of 1.5 cm and a pitch of 1.7 cm, covering an area of about 20 cm 20 cm. A cardboard mask with a square opening of 10 cm by 10 cm was placed thereon and slight vacuum was applied from underneath the support board for the set of helical springs to ease flat positioning of the topsheet layer.

A piece of 12 cm by 12 cm of commercially available high-loft polyester fibre air-through bonded nonwoven, Paratherm Loft VTF 273 at 90 g/m², available from TWE Dierdorf, Germany, was placed centred over the mask.

4 g of conventional SAP particles of the Type EK-X EN67 available from EKTOTEC GmbH, Haan, Germany, have been manually sprinkled evenly over the mask area of 10 cm by 10 cm. A portion of the SAP particles penetrated into the high loft material. A small portion remained on the surface, and another small portion penetrated through the high-loft web and retained by the topsheet material.

A second topsheet layer 20 cm by 20 cm was positioned over the surface of the high-loft material.

By means of a manual ultrasonic welding sonotrode, the three webs were meltfusion bonded at the uppermost support points of the helical springs, thereby creating elliptical bonding points of approximately 1.5 mm length and about 0.5 mm width.

Due to the compression required for the bonding, a soft quilted structure resulted.

A second ultrasonic bond line was made circumferentially outwardly of the sandwich region, forming a 15 cm by 15 cm square.

Both samples were evaluated by being loaded with 0.9% saline solution.

To this end, the samples were placed in a dish of 40 by 40 cm with the first topsheet side down. 120 ml of 0.9% saline solution were added to the dish and the swelling of the structures was observed.

For the comparative sample, most of the bonding points remained bonded, and a strongly quilted structure resulted.

For the inventive sample most of the bonding points de-bonded, the structure expanded z-directionally, thereby pulling the outward second ultrasonic bond line inwardly without de-bonding it.

Both samples were left until they reached equilibrium after 5 minutes.

Unabsorbed liquid was decanted and weighed: For the comparative sample 51 ml were not absorbed, for the inventive example 33 ml were not absorbed.

Further a sharp pair of scissors was used to open all quilt regions, and the decanted liquid was re-filled into the dish.

The samples were left for another 5 minutes and the unabsorbed liquid was decanted. For the comparative example 23 ml were decanted, for the inventive sample 22 ml.

After finishing of the test, the comparative sample did not exhibit any structural integrity, i.e. the nonwoven webs did not retain any of the swollen particles.

The inventive sample could be lifted from the dish essentially without losing any of the swollen particles.

This tests shows how the sandwich structure exhibits a strongly quilted structure limiting the absorption of liquid. In contrast, the inventive structure proved a smooth surface and exhibits better absorbency properties and good structural integrity.

Test Methods

The measurements should, unless stated otherwise, be carried out at an ambient temperature of 23±2° C. and a relative atmospheric humidity of 50±10%. The water-absorbent polymers are mixed thoroughly before the measurement.

Saline Flow Conductivity (SFC)

The saline flow conductivity is, as described in EP 0 640 330 A1, determined as the gel layer permeability of a swollen gel layer of water-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface.

The procedure and the evaluation of the measurement remains unchanged from EP 0 640 330 A1, except for using 0.9% saline solution instead of Jayco Synthetic Urine. The flow rate is recorded automatically.

The saline flow conductivity (SFC) is calculated as follows:

$$SFC[cm^3 s/g] = (Fg(t=0) \times L0)/(d \times A \times WP),$$

where $Fg(t=0)$ is the flow rate of NaCl solution in g/s, which is obtained by means of a linear regression analysis of the $Fg(t)$ data of the flow determinations by extrapolation to $t=0$, L0 is the thickness of the gel layer in cm, d is the density of the NaCl solution in g/cm³, A is the surface area of the gel layer in cm² and WP is the hydrostatic pressure over the gel layer in dyn/cm².

Centrifuge Retention Capacity (CRC)

The centrifuge retention capacity of the water-absorbent polymer particles is determined by the EDANA recommended test method No. WSP 241.2-05 "Centrifuge Retention Capacity", wherein for higher values of the centrifuge retention capacity lager tea bags have to be used.

Absorbency Under High Load (AUHL)

The absorbency under high load of the water-absorbent polymer particles is determined analogously to the EDANA recommended test method No. WSP 242.2-05 "Absorption Under Pressure", except using a weight of 49.2 g/cm² instead of a weight of 21.0 g/cm². The EDANA test methods are obtainable, for example, from the EDANA,—Avenue Herrmann Debroux, 46; B-1160 Brussels, Belgium.

The invention claimed is:
1. A method for the manufacture of an absorbent structure, said structure comprising
  fibres forming a fibrous matrix having an x-, y-, and thickness or z-extension;
  superabsorbent polymer (SAP) particles which are capable of exerting an expansion force upon swelling upon absorption of a liquid and which are positioned within the pores of said fibrous matrix;
  at least one cover web,
  and meltfusion bond points arranged in an x-y-directionally extending bonding pattern, penetrating z-directionally through said fibrous matrix,
said method comprising the steps of
  providing a fibrous matrix;
  providing SAP particles;

positioning said SAP particles in interfibre pores of said matrix at a basis weight of not less that about 50 g/m$^2$;

providing at least one cover web;

providing a support structure;

positioning said fibrous matrix with said SAP particles and said at least one cover web positioned parallel to both x-y-directionally extending surface of said structure on said support structure; applying energy to said structure to form meltfusion points in a predetermined pattern determined by said support structure, wherein said meltfusion points connect said cover web positioned on both surfaces of said structure and exhibit an aspect ratio of their long axis to their short axis of at least 1.05 to 1 and wherein said meltfusion bonds are essentially free of particulate SAP.

2. A method according to claim 1, wherein said support structure is in the form of a flexible anvil.

3. A method according to claim 1, wherein said support structure is in the form of helical anvil.

4. A method for forming an absorbent structure according to claim 1, wherein said energy is ultrasonic energy.

5. A method for forming an absorbent structure according to claim 1, wherein said meltfusion points form a predetermined x-y-directional bond point pattern.

6. A method for forming an absorbent structure according to claim 5, wherein said meltfusion points form a predetermined x-y-directional bond point pattern satisfying at least one of the conditions selected from the group consisting of the bond points have a bond point size of from about 0.1 mm$^2$ to about 20 mm$^2$;

the bond points exhibit an ellipsoidal shape;

the number of bond points in the pattern is from one bond point per 9 cm$^2$ to 1 bond point per 9 mm$^2$;

the bonding pattern comprises one or more sub-pattern.

7. A method for forming an absorbent structure according to claim 1, wherein said fibrous matrix is provided as one or more prebonded web(s).

8. A method for forming an absorbent structure according to claim 1, wherein said positioning of said particles in said web is aided by an embedding aiding means comprising one or more elements selected from the group consisting of vacuum;

tentering x- or y-directionally;

mechanically activating between two flat, profiled or interdigitizing rolls;

shaking or vibrating.

9. A method for forming an absorbent structure according to claim 1, further comprising one or more of the steps selected from the group consisting of applying one or more secondary containment means, circumscribing said absorbent structure x-y-directionally;

applying an expansion aiding means;

providing the SAP particles in an essentially continuous stream, which is modulated, before said particles are positioned in the interfibre pores.

10. A method for forming an absorbent structure according to claim 9, wherein said secondary containment means is a circumferential bonding, exhibiting a bond strength higher than the bond strength of said meltfusionable bond points.

11. A method for forming an absorbent structure according claim 9, wherein said expansion aiding means is a circumferential fold line or a pop open line.

12. A method for forming an absorbent structure according to claim 9, wherein said modulated continuous stream of SAP particles is interrupted before said particles are positioned in the interfibre pores.

* * * * *